United States Patent
Yigal et al.

(10) Patent No.: US 11,389,598 B2
(45) Date of Patent: Jul. 19, 2022

(54) NEEDLE SHIELD FOR INJECTION NEEDLE RETRACTION

(71) Applicant: West Pharma. Services IL, Ltd., Ra'anana (IL)

(72) Inventors: Gil Yigal, Gan Yavne (IL); Yossi Bar-El, Beit Arye (IL)

(73) Assignee: West Pharma. Services IL, Ltd., Ra'anana (IL)

( * ) Notice: Subject to any disclaimer, the term of this patent is extended or adjusted under 35 U.S.C. 154(b) by 25 days.

(21) Appl. No.: 16/617,819

(22) PCT Filed: May 30, 2018

(86) PCT No.: PCT/US2018/035000
§ 371 (c)(1),
(2) Date: Nov. 27, 2019

(87) PCT Pub. No.: WO2018/222636
PCT Pub. Date: Dec. 6, 2018

(65) Prior Publication Data
US 2020/0188608 A1    Jun. 18, 2020

Related U.S. Application Data

(60) Provisional application No. 62/512,474, filed on May 30, 2017.

(51) Int. Cl.
*A61M 5/32* (2006.01)

(52) U.S. Cl.
CPC ........ *A61M 5/3232* (2013.01); *A61M 5/3202* (2013.01); *A61M 5/3219* (2013.01); *A61M 5/3245* (2013.01); *A61M 5/3293* (2013.01)

(58) Field of Classification Search
CPC ........... A61M 2005/14256; A61M 2005/1426; A61M 2005/3212; A61M 5/3232;
(Continued)

(56) References Cited

U.S. PATENT DOCUMENTS

| | | |
|---|---|---|
| 5,346,086 A | 9/1994 | Harris |
| 2009/0198215 A1 | 8/2009 | Chong et al. |

(Continued)

FOREIGN PATENT DOCUMENTS

| | | |
|---|---|---|
| CN | 1355716 A | 6/2002 |
| CN | 2748099 Y | 12/2005 |

(Continued)

OTHER PUBLICATIONS

Office Action dated Dec. 15, 2020 in Japanese Application No. 2019-566222.

(Continued)

*Primary Examiner* — Bhisma Mehta
*Assistant Examiner* — Robert F Allen
(74) *Attorney, Agent, or Firm* — BakerHostetler

(57) ABSTRACT

An injector includes a housing, a needle hub movably mounted within the housing and an injection needle supported by the hub. The hub and the needle are axially translatable between retracted and injection positions. A needle shield, having an aperture, is movably connected to the housing between first and second positions. The needle extends through the needle shield aperture in the injection position of the needle and the first position of the needle shield, and the needle is blocked from extending through the needle shield aperture in the second position of the needle shield. When the needle shield is in the second position and the hub and the needle are in the injection position, the needle shield covers the tip of the needle and subsequent movement of the needle shield toward the first position axially translates the hub and the needle back toward the retracted position.

40 Claims, 6 Drawing Sheets

(58) Field of Classification Search
CPC .............. A61M 5/3234; A61M 5/3205; A61M 5/3212; A61M 5/3202; A61M 5/3219; A61M 5/3245; A61M 5/3293; A61M 5/14244; A61M 5/322
See application file for complete search history.

(56) References Cited

U.S. PATENT DOCUMENTS

| | | | |
|---|---|---|---|
| 2013/0253434 A1* | 9/2013 | Cabiri | A61M 5/1626 604/192 |
| 2013/0296785 A1* | 11/2013 | Cabiri | A61M 5/2033 604/151 |
| 2014/0052072 A1 | 2/2014 | Simas, Jr. et al. | |
| 2014/0228780 A1 | 8/2014 | Cabiri | |
| 2015/0250946 A1 | 9/2015 | Cabiri | |
| 2016/0193406 A1 | 7/2016 | Cabiri | |

FOREIGN PATENT DOCUMENTS

| | | |
|---|---|---|
| CN | 1921900 A | 2/2007 |
| CN | 101573155 A | 11/2009 |
| CN | 101868269 A | 10/2010 |
| CN | 102883759 A | 1/2013 |
| CN | 104245018 A | 12/2014 |
| CN | 104321100 A | 1/2015 |
| CN | 104379196 A | 2/2015 |
| CN | 104759006 A | 7/2015 |
| CN | 104812428 A | 7/2015 |
| CN | 105107065 A | 12/2015 |
| CN | 105816942 A | 8/2016 |
| JP | 2004501721 A | 1/2004 |
| JP | 2006501043 A | 1/2006 |
| JP | 2013517094 A | 5/2013 |
| JP | 2015166048 A | 9/2015 |
| WO | 0202165 A2 | 1/2002 |
| WO | 2004032990 A2 | 4/2004 |
| WO | 2005/018703 A2 | 3/2005 |
| WO | 2011090955 A1 | 7/2011 |
| WO | 2017210448 A1 | 12/2017 |

OTHER PUBLICATIONS

Int'l Search Report and Written Opinion dated Aug. 6, 2018 in Int'l Application No. PCT/US2018/035000.
Office Action dated Jun. 3, 2021 in Chinese Office Action 201880034803.5.

* cited by examiner

NEEDLE SHIELD FOR INJECTION NEEDLE RETRACTION

CROSS-REFERENCE TO RELATED APPLICATIONS

This application is a section 371 of International Application No. PCT/US2018/035000, filed May 30, 2018, which was published on Dec. 6, 2018 under International Publication No. WO 2018/222636 A1, and which claims priority from U.S. Provisional Patent Application No. 62/512,474, titled "Needle Shield Safety Latch Lock to Needle Hub", filed on May 30, 2017, the entire contents of each of which are incorporated by reference herein.

BACKGROUND OF THE DISCLOSURE

The present disclosure is generally directed to a needle shield, and, more particularly, to a needle shield employed in an injector for covering and retracting an injection needle post injection.

An injector, such as, for example, a drug injector, is typically engaged with a user's skin to perform an injection. Thereafter, the injector is withdrawn from the user's skin, leaving the injection needle thereof exposed. It is well documented that exposure of a used needle is dangerous as an individual (whether the user or another individual) may be pricked by the exposed, used needle, causing injury or harm, whether by the physical prick, by exposing an individual to a drug that may cause a reaction, or by blood transmitted disease.

In certain prior wearable injector devices, the injection needle is non-retractable, but rather a needle shield is employed to cover the injection needle after injection. The needle shield may be maintained propped open by the injection needle. Subsequent collapse of the needle shield bends the injection needle into a secure area within the needle shield. In rare cases, however, it has been found that bending of the needle may nevertheless potentially result in a stick hazard.

Therefore, it would be advantageous to manufacture an injector having a needle shield, together configured such that collapse of the needle shield predominantly retracts the injection needle back toward the retracted (pre-injection) position thereof.

BRIEF SUMMARY OF THE DISCLOSURE

Briefly stated, one aspect of the present disclosure is directed to an injector comprising an injector housing having a surface configured to contact a skin surface of a user, the surface having an opening therein. A needle hub is movably mounted within the injector housing and an injection needle is supported by the movable needle hub. The needle hub and the injection needle are axially translatable between a retracted position, wherein at least a tip of the injection needle is contained within the injector housing, and an injection position, wherein at least the tip of the injection needle protrudes from the injector housing. A biasing member is operatively connected with the injection needle to axially translate the needle hub and the injection needle from the retracted position to the injection position. The injector further comprises a needle shield having an aperture, the needle shield being movably connected to the injector housing and movable between a first position and a second position. The injection needle extends through the needle shield aperture in the injection position of the injection needle and the first position of the needle shield, and the injection needle is blocked from extending through the needle shield aperture in the second position of the needle shield. When the needle shield is in the second position and the needle hub and the injection needle are in the injection position, the needle shield covers the tip of the injection needle and subsequent movement of the needle shield toward the first position axially translates the needle hub and the injection needle back toward the retracted position.

Another aspect of the disclosure is directed to an injector comprising an injector housing having a surface configured to contact a skin surface of a user, the surface having an opening therein. An injection needle is movably mounted within the injector housing, and is axially translatable between a retracted position, wherein at least a tip of the injection needle is contained within the injector housing, and an injection position, wherein at least the tip of the injection needle protrudes from the injector housing. A needle shield is movably connected to the injector housing and movable between a first position and a second position. The needle shield includes an aperture and a cantilevered arm, the cantilevered arm having a flanged free end partially blocking the needle shield aperture. The flanged free end clears the injection needle in the first position of the needle shield, permitting the injection needle to extend through the needle shield aperture in the first position of the needle shield. When the needle shield is in the second position and the injection needle is in the injection position, the needle shield covers the tip of the injection needle and the flanged free end of the cantilevered arm blocks extension of the injection needle through the needle shield aperture.

BRIEF DESCRIPTION OF THE DRAWINGS

The following detailed description of aspects of the disclosure will be better understood when read in conjunction with the appended drawings. It should be understood, however, that the disclosure is not limited to the precise arrangements and instrumentalities shown. In the drawings.

DETAILED DESCRIPTION OF THE DISCLOSURE

Figure 1:
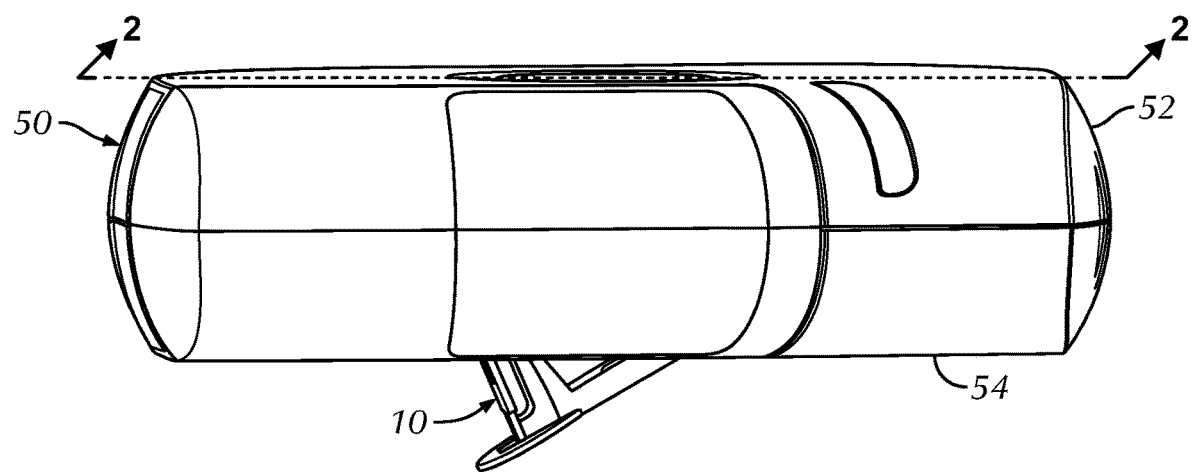
FIG. 1 is an elevational view of a wearable injector, having a needle shield in accordance with a first embodiment of the present disclosure movably mounted thereto.

Certain terminology is used in the following description for convenience only and is not limiting. The words "lower," "bottom," "upper" and "top" designate directions in the drawings to which reference is made. The words "inwardly," "outwardly," "upwardly" and "downwardly" refer to directions toward and away from, respectively, the geometric center of the injector, and designated parts thereof, in accordance with the present disclosure. Unless specifically set forth herein, the terms "a," "an" and "the" are not limited to one element, but instead should be read as meaning "at least one." The terminology includes the words noted above, derivatives thereof and words of similar import.

It should also be understood that the terms "about," "approximately," "generally," "substantially" and like terms, used herein when referring to a dimension or characteristic of a component of the disclosure, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to the drawings in detail, wherein like numerals indicate like elements throughout, there is shown in FIGS. 1-8 an injection needle shield, generally designated 10, in accordance with a first embodiment of the present disclosure. Generally, the injection needle shield 10 is employed with a wearable injector (patch injector) 50, such as, for example, without limitation, a wearable drug injector, but the disclosure is not so limited. At a minimum, the injection needle shield 10 may alternatively be employed in other injector configurations.

Figure 2:
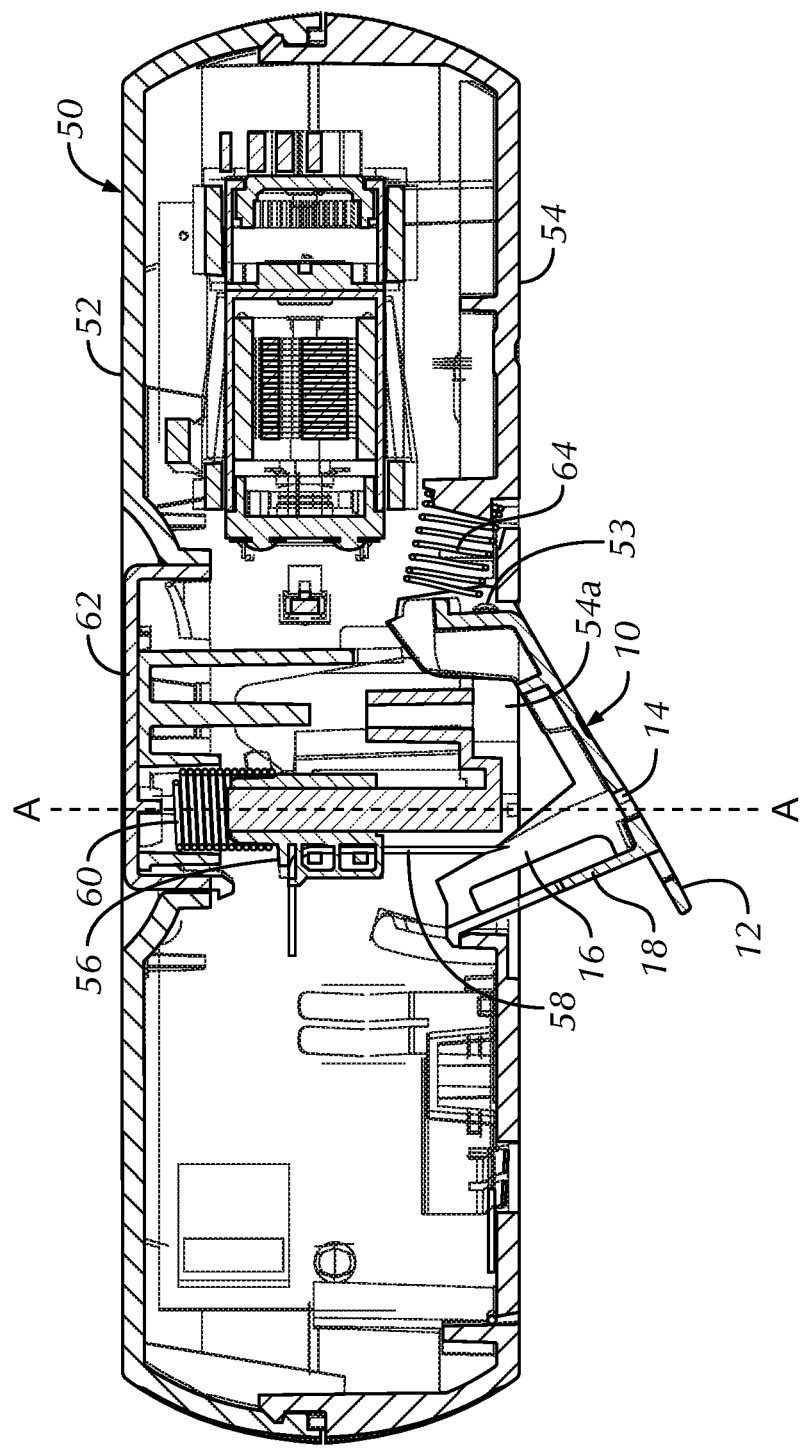
FIG. 2 is a cross-sectional view of the injector and needle shield of FIG. 1, taken along the sectional line 2-2 of FIG. 1, with an injection needle of the injector in a retracted position thereof and the needle shield in a second position thereof.

As should be understood by those of ordinary skill in the art, and as best shown in FIG. 2, an injector 50 generally comprises a housing 52 having a surface 54 configured to contact a skin surface of a user (not shown), e.g., a patient, the surface 54 having an opening 54a therein. As shown, a needle hub 56, e.g., a polymeric needle hub 56, is movably mounted within the injector housing 52 and an injection needle 58 is supported by the movable needle hub 56. In one non-limiting example, the injection needle 58 may be at least a 27 gauge needle. The needle hub 56 and the injection needle 58 are axially translatable along an axis A, extending substantially perpendicularly to the surface 54, between a retracted position (FIG. 2), wherein at least a tip 58a of the injection needle 58 is contained within the injector housing 52, and an injection position (FIGS. 4-6), wherein at least the tip 58a of the injection needle 58 protrudes from the injector housing 52 through the opening 54a and through an aperture 14 of the needle shield 10 (as will be explained in further detail below).

Figure 4:
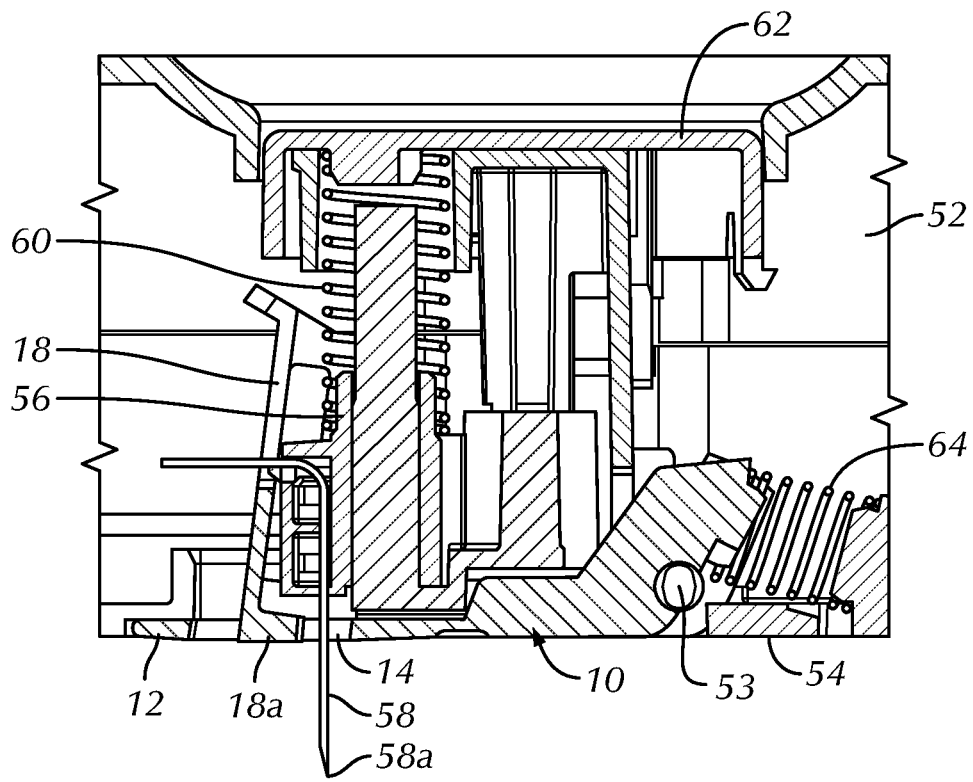
FIG. 4 is an enlarged, partial cross-sectional view of the injector and needle shield of FIG. 1, taken along the sectional line 2-2 of FIG. 1, with the injection needle in a injection position thereof and the needle shield in a first position thereof.

A biasing member 60 is operatively connected with the injection needle 58 to drive the needle hub 56 and the injection needle 58 from the retracted position to the injection position. In the illustrated embodiment, the biasing member 60 takes the form of a coil spring expandable from a contracted state (FIG. 2) to an expanded state (FIG. 4). In the illustrated embodiment, the coil spring 60 is mounted between the needle hub 56 and a depressible activation button assembly 62 of the injector 50, i.e., the spring 60 abuts the activation button assembly 62 at one end and abuts the needle hub 56 at an opposing end. In the contracted, i.e., energy storing, state thereof, the coil spring 60 is prevented from driving the needle hub 56 and the injection needle 58 into the injection position. Upon release into the expanded, i.e., an energy releasing, state thereof (generally by depressing the activation button assembly 62), the coil spring 60 drives the needle hub 56 and the injection needle 58 into the injection position. As should be understood by those of ordinary skill in the art, the biasing member 60 may alternatively take the form of other members capable of storing and releasing a biasing force. Non-limiting examples include other springs (e.g., torsion or leaf springs), elastic bands, and the like. Alternatively, the biasing member 60 may take the form of an actuator configured to apply a translational force onto the needle hub 56 and the injection needle 58.

Figure 7:
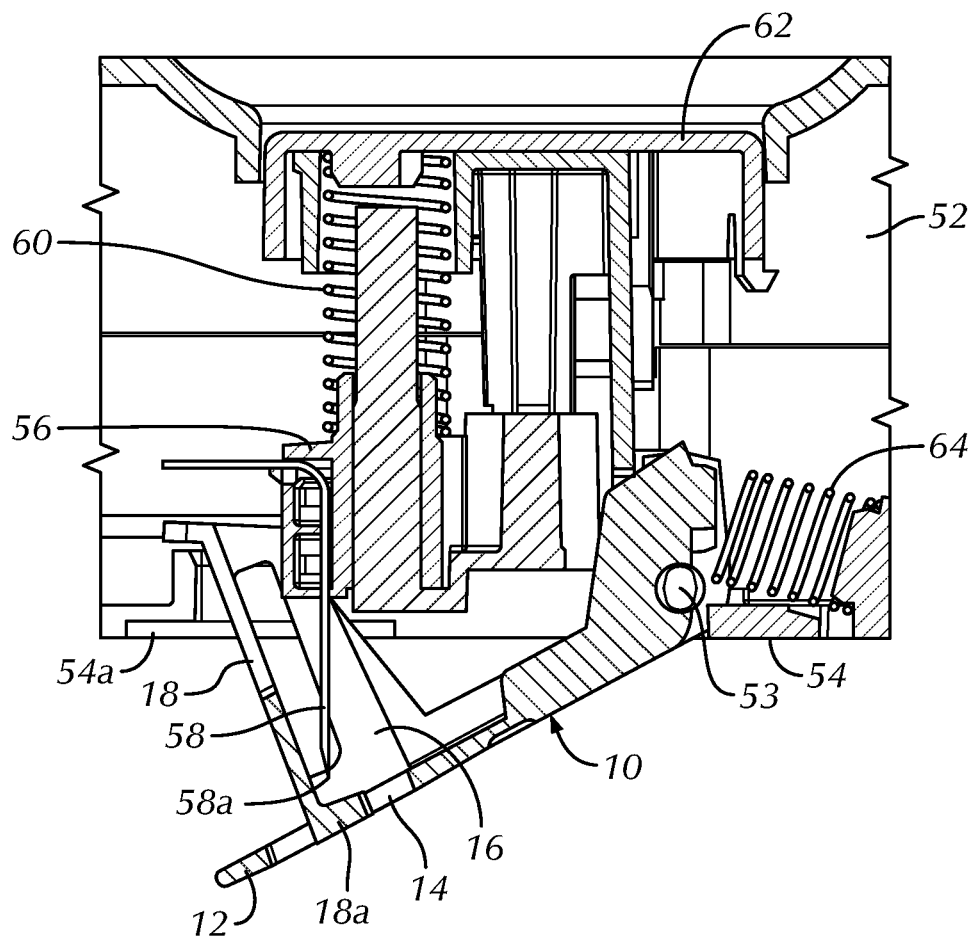
FIG. 7 is an enlarged, partial cross-sectional view of the injector and needle shield of FIG. 1, taken along the sectional line 2-2 of FIG. 1, with the injection needle in the injection position thereof and the needle shield in the second position thereof.

Turning to the needle shield 10, the needle shield 10, e.g., a polymeric needle shield 10, is movably connected to the injector housing 52 in a manner well understood by those of ordinary skill in the art. In the illustrated embodiment, the needle shield 10 is pivotably attached to the injector housing 52, e.g., via a pin connector 53 proximate an end of the needle shield 10, proximate the opening 54a of the skin contacting surface 54. The needle shield 10 is movable between a first position and a second position. In the first position (FIG. 4), the needle shield 10 extends generally flush with the skin contacting surface 54 of the injector 50, but the disclosure is not so limited. In the second position (FIGS. 1, 2, 7), the needle shield 10 is pivoted away, i.e., downwardly, with respect to the axis A, from the skin contacting surface 54. In the second position, the aperture 14 of the needle shield 10 is elevationally lower than the tip 58a of the injection needle 58, with respect to the axis A, in any position of the injection needle 58. As will be explained in further detail below, when the needle shield 10 is in the second position and the injection needle 58 is in the injection position, the needle shield 10 covers the tip 58a of the injection needle 58 (FIG. 7). In the illustrated embodiment, the needle shield 10 is biased by a coil spring 64 to the second position thereof, but the disclosure is not so limited. Alternatively, the needle shield 10 may be biased into the second position thereof by another form of biasing member (such as, for example, without limitation, as identified above as alternative biasing members 60) or merely by gravitational force.

Figure 3:
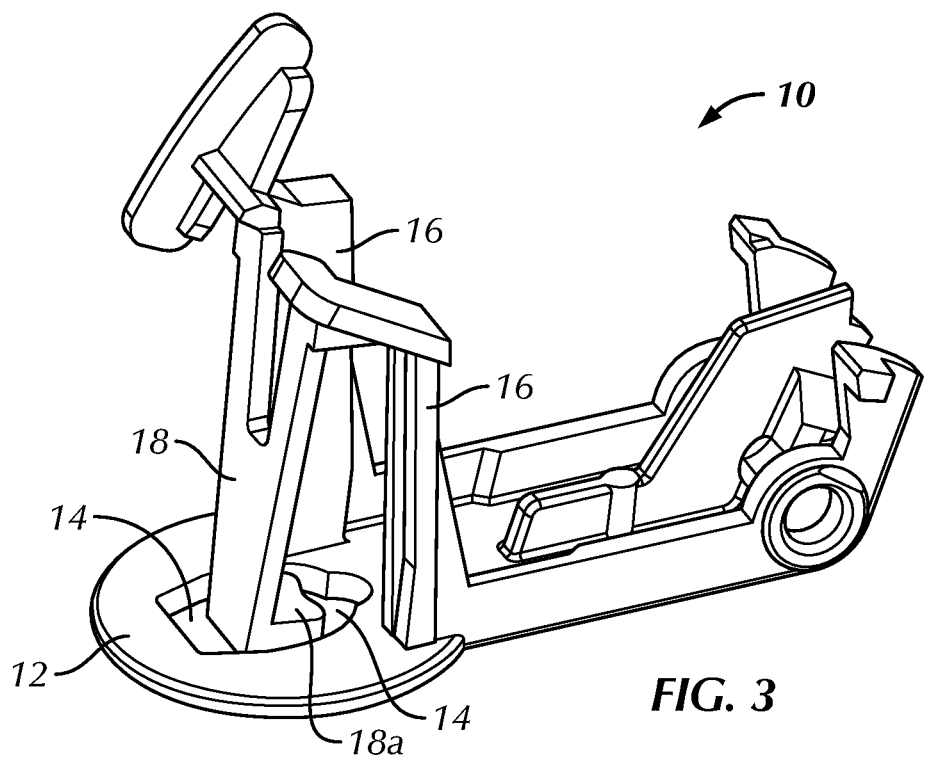
FIG. 3 is a top and side perspective view of the needle shield of FIG. 1.

As shown best in FIG. 3, the needle shield 10 includes a base surface 12 defining the aperture 14 therein. The needle shield 10 further includes at least one post 16 (a pair of posts 16 in the illustrated embodiment) extending upwardly from the base surface 12. A cantilevered arm 18 extends downwardly from the post(s) 16 toward the base surface 12. The cantilevered arm 18 includes a flanged free end 18a, i.e., the free end of the arm 18 comprises a flange 18a extending generally laterally relative to the arm 18. The cantilevered arm 18 is dimensioned such that the flanged end 18a is positioned in the needle shield aperture 14 and the laterally extending flange 18a is angled to extend substantially along the same plane as the plane of extension of the base surface 12, thereby partially blocking the needle shield aperture 14.

Prior to placement of the injector 50 on the skin surface of a user, the injection needle 58 is blocked from extending through the needle shield aperture 14 (FIG. 2). That is, when the needle shield 10 is in the second position, the injection needle 58 is either not axially aligned with the aperture 14 or the flanged free end 18a of the cantilevered arm 18 blocks the pathway of the injection needle 58 through the aperture 14. Conversely, when the injector 50 is placed on the skin surface of a user (prior to injection), moving the needle shield 10 to the first position thereof (against the force biasing the needle shield 10 into the second position), the needle shield aperture 14 axially aligns with the injection needle 58. That is, when the needle shield 10 is moved to the first position thereof and the injection needle 58 is in the retracted position thereof, a portion of the needle shield aperture 14 unblocked by the flanged free end 18a of the cantilevered arm 18 is axially aligned with the injection needle 58. The flanged end 18a clears the injection needle 58 in such configuration. Accordingly, when the injector 50 is placed on the user's skin surface, the injection needle 58 may be moved to the injection position (FIG. 4), such that the injection needle 58 extends through the opening 54a of the injector 50, through the needle shield aperture 14 and into the user as the injection needle 58 is driven into the injection position thereof.

After injection, e.g., of medicament, is complete, the user (or another individual) removes the injector 50 from the skin surface of the user. Accordingly, as the injector 50 is removed from the skin surface (and while the injection needle 58 remains in the injection position thereof), the biasing force (either gravitational force or the biasing force of the spring 64) also returns the needle shield 10 to the second position thereof. Progressive movement of the needle shield 10 under the biasing force from the first position (where the injection needle 58 is aligned with an unblocked portion of the needle shield aperture 14) to the second position (wherein the injection needle 58 is either not axially aligned with the needle shield aperture 14 or the flanged free end 18a of the cantilevered arm 18 blocks the pathway of the injection needle 58 through the aperture 14) progressively moves at least the unblocked portion of the needle shield aperture 14 out of axial alignment with the injection needle 58.

Figure 5:
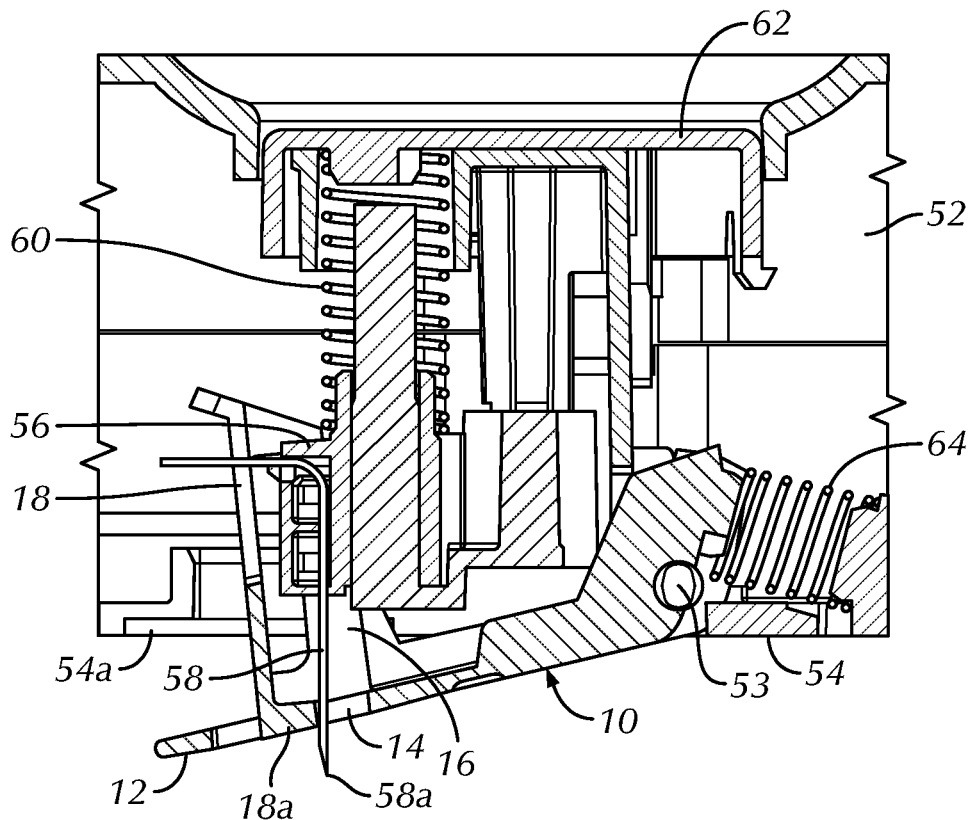
FIG. 5 is an enlarged, partial cross-sectional view of the injector and needle shield of FIG. 1, taken along the sectional line 2-2 of FIG. 1, with the injection needle in the injection position thereof and the needle shield returning from the first position thereof to the second position thereof.
Figure 6:
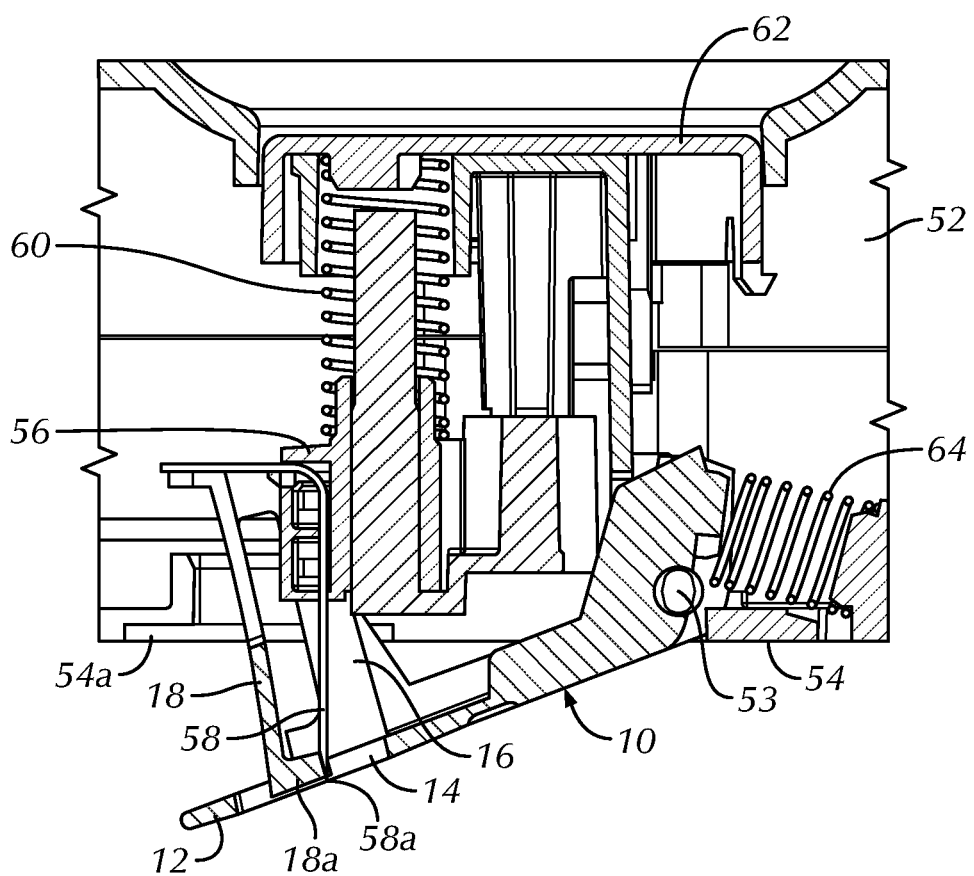
FIG. 6 is an enlarged, partial cross-sectional view of the injector and needle shield of FIG. 1, taken along the sectional line 2-2 of FIG. 1, with the injection needle in the injection position thereof and the needle shield further traveled from the first position thereof to the second position thereof relative to FIG. 5.

As shown between FIGS. 5 and 6, the flanged end 18a of the cantilevered arm 18 comes into contact with the injection needle 58 during needle shield 10 movement from the first position (FIG. 4) toward the second position (FIG. 7) with the injection needle 58 in the injection position. The cantilevered arm 18 is constructed to be elastically flexible, and is more flexible than the injection needle 58. That is, the injection needle 58 is constructed to define a greater bending stiffness, i.e., resistance against bending deformation, than the cantilevered arm 18, in a manner well understood by those of ordinary skill in the art. For example, the cantilevered arm 18 may be constructed of a polymeric material and the injection needle 58 may be constructed of a metal material that exhibits a greater bending stiffness than the bending stiffness of the polymeric material of the cantilevered arm 18. The cantilevered arm 18 is, therefore, more deflectable than the injection needle 58.

Accordingly, when the injection needle 58 is in the injection position and comes into contact with the flanged end 18a of the cantilevered arm 18 (FIG. 5), as the needle shield 10 moves from the first position back to the second position, the injection needle 58 deflects (FIG. 6), i.e., elastically flexes, the cantilevered arm 18 out of an unflexed resting position thereof. Deflection of the cantilevered arm 18 temporarily moves the flanged end 18a aside, enlarging the unblocked portion of the needle shield aperture 14, to permit the needle shield 10 to pivot beyond the injection needle 58 and reach the second position thereof. As the needle shield 10 clears the tip 58a of the injection needle 58 and the injection needle 58 disengages the cantilevered arm 18, the cantilevered arm 18 returns to the unflexed resting position thereof (FIG. 7). As shown in FIG. 7, return of the cantilevered arm 18 to the unflexed resting position thereof when the needle shield 10 returns to the second position thereof results in the flanged free end 18a of the cantilevered arm 18 returning to blocking the pathway of the injection needle 58 through the needle shield aperture 14.

As explained previously, the needle shield 10 covers the tip 58a of the injection needle 58 when the needle shield 10 is in the second position and the injection needle 58 is in the injection position, thereby protecting the user or other individual from inadvertent contact with the tip 58a of the used injection needle 58 that may otherwise injure or infect the individual. After the injector 50 is removed from the skin surface of the user, and the needle shield 10 returns to the second position thereof to cover the injection needle tip 58a, however, inadvertent subsequent contact with the needle shield 10 with a force countering and overcoming the biasing force of the spring 64 moves the needle shield 10 back toward the first position thereof, i.e., collapse the needle shield.

Figure 8:
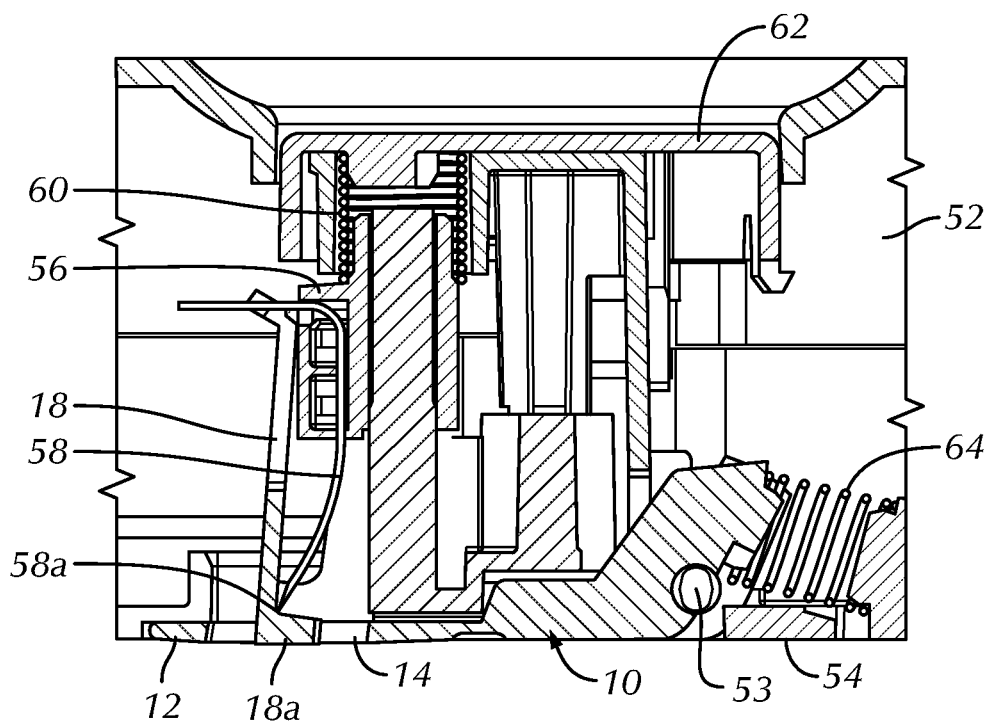
FIG. 8 is an enlarged, partial cross-sectional view of the injector and needle shield of FIG. 1, taken along the sectional line 2-2 of FIG. 1, with needle shield moved from the second position thereof substantially back to the first position thereof and axially translating the injection needle therewith substantially back to the retracted position thereof.

As shown in FIG. 8, subsequent collapse of the needle shield 10 from the second position toward the first position thereof, advantageously axially translates the needle hub 56 and the injection needle 58 back toward the retracted position thereof to preclude the injection needle 58 from potentially extending beyond the needle shield 10. As shown in FIG. 8, the flanged free end 18a of the cantilevered arm 18 directly contacts the injection needle 58, e.g., contacts the tip 58a, upon such movement. In some embodiments, the injection needle 58 defines a greater stiffness than the stiffness of the coil spring 60 in a manner well understood by those of ordinary skill in the art. For example, the injection needle 58 may be constructed of a material that defines a stiffness greater than a stiffness of the coil spring 60 and/or a coil spring 60 may be selected that defines a weaker stiffness than the injection needle 58.

Accordingly, as shown in FIG. 8, contact of the needle shield 10 with the injection needle 58 during subsequent collapse of the needle shield 10 from the second position to the first position pushes the injection needle 58 and the needle hub 56 back toward the retracted position thereof, compressing the coil spring 60 back toward the contracted state, rather than merely bending the injection needle 58. In some cases, the injection needle 58 may also bend at least slightly, while moving back toward the injector housing 52 in addition to predominantly contracting the coil spring 60 to retract the needle hub 56 and the injection needle 58. Alternatively, the injection needle 58 may be supported against bending to cause retraction of the needle hub 56 and the injection needle 58 rather than bending of the injection needle 58. For example, the cantilevered arm 18 may be positioned to reduce or prevent bending of the injection needle 58. As should be understood by those of ordinary skill in the art, however, the needle shield 10 may be configured such that a different portion of the shield 10, e.g., the base surface 12, contacts the injection needle 58 upon such movement to axially translate the needle hub 56 and the injection needle 58 back toward the retracted position.

Figure 9:
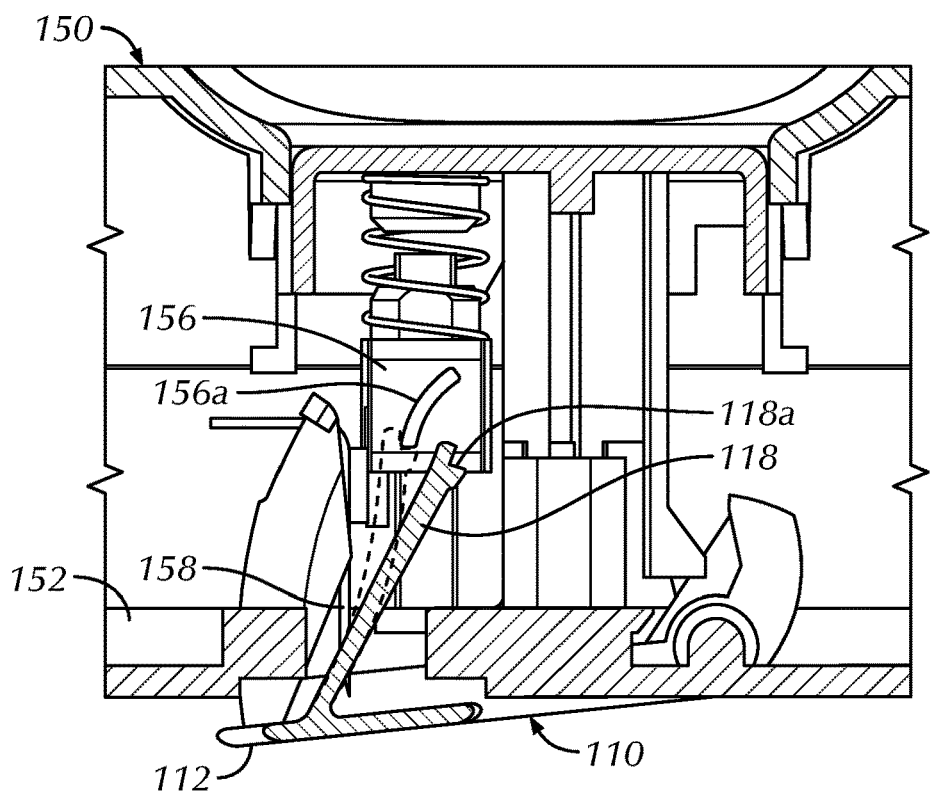
FIG. 9 is an enlarged, partial cross-sectional view of the an injector and a needle shield in accordance with a second embodiment of the present disclosure, taken along the sectional line 2-2 of FIG. 1, with the needle hub being retracted by the needle shield (in broken line) and the needle hub clearing the needle shield (in solid line)
Figure 10:
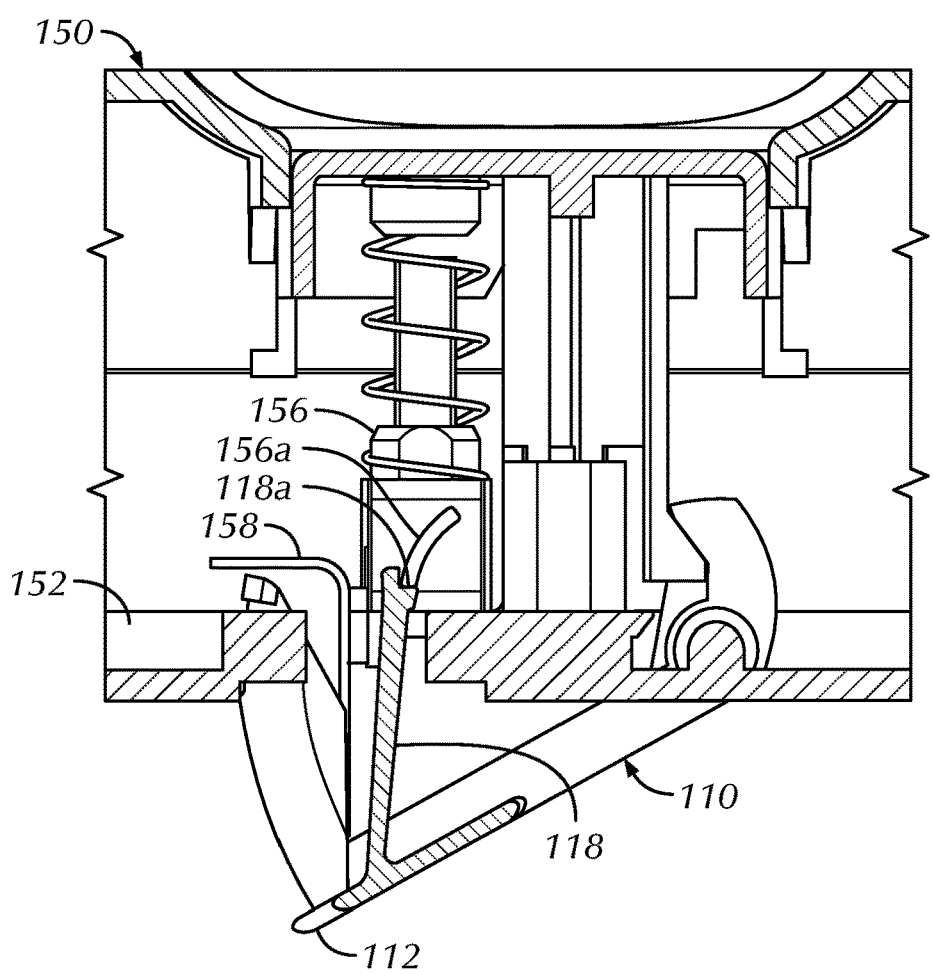
FIG. 10 is an enlarged, partial cross-sectional view of the injector and the needle shield of FIG. 9, taken along the sectional line 2-2 of FIG. 1, with needle shield being moved from the second position thereof back to the first position thereof and axially translating the needle hub therewith back to the retracted position thereof.

FIGS. 9-10 illustrate a second embodiment of the needle shield 110. The reference numerals of the second embodiment (for both the injector 150 and the needle shield 110) are distinguishable from those of the above-described first embodiment (FIGS. 1-8) by a factor of one-hundred (100), but otherwise indicate the same elements as indicated above, except as otherwise specified. The needle shield 110 of the present embodiment is substantially similar to that of the earlier embodiment. Therefore, the description of certain similarities and modes of operation between the embodiments may be omitted herein for the sake of brevity and convenience, and, therefore, is not limiting.

One difference of the needle shield 110 over the embodiment of FIGS. 1-8, is that when the needle shield 110 is in the second position thereof and the needle hub 156 and the injection needle 158 are in the injection position, movement of the needle shield 110 back toward the first position indirectly axially translates (retracts) the injection needle 158 back toward the retracted position.

As shown in FIGS. 9 and 10, the needle shield 110 comprises a cantilevered arm 118 extending upwardly from the base surface 112 of the needle shield 110 toward the needle hub 156. The cantilevered arm 118 defines a flanged free end 118a at an upper end thereof. That is, a flange 118a extends laterally from the cantilevered arm 18 at, or proximate, the upper free end thereof. The cantilevered arm 118 is configured to engage the needle hub 156, rather than the injection needle 158, during movement of the needle shield 110 from the second position thereof toward the first position thereof when the injection needle 158 is in the injection position, thereby axially translating the needle hub 156 back into the injector housing 152 to retract the needle hub 156 and the injection needle 158.

Conversely, prior to injection (FIG. 9—arm 118 drawn in solid line), the needle hub 156 clears the cantilevered arm 118. That is, the cantilevered arm 118 is positioned such that when the needle hub 156 and the injection needle 158 are in the retracted position, the cantilevered arm 118 does not engage, or otherwise interfere with, the needle hub 156 during movement of the needle shield 110 from the second position thereof to the first position thereof, e.g., while initially placing the injector 150 on the body of the user. Thereafter the cantilevered arm 118 also does not interfere with movement of the needle hub 156 and the injection needle 158 from the retraction position to the injection position for injection.

After injection, when the injector 150 is removed from the user's skin and the needle shield 110 has returned to the second position thereof, if the needle shield 110 is pushed back toward the first position, as shown in FIG. 10, the cantilevered arm 118 contacts the needle hub 156 and retracts the needle hub 156 and the injection needle 158 toward the retracted position (FIG. 9—arm 118 drawn in broken lines). In the illustrated embodiment, the needle hub 156 comprises a flanged member 156a extending therefrom configured to engage the flanged end 118a of the cantilevered arm 118, but the disclosure is not so limited.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the present disclosure, as set forth in the appended claims.

We claim:

1. An injector comprising:
an injector housing having a surface configured to contact a skin surface of a user, the surface having an opening therein;
a needle hub movably mounted within the injector housing;
an injection needle supported by the movable needle hub, the needle hub and the injection needle being axially translatable between a retracted position, wherein at least a tip of the injection needle is contained within the injector housing, and an injection position, wherein at least the tip of the injection needle protrudes from the injector housing; and
a needle shield having a base surface defining an aperture therein and a cantilevered arm extending from the base surface, the cantilevered arm including a flanged free end configured to engage with the needle hub, the needle shield being movably connected to the injector housing and movable between a first position and a second position, wherein:
the needle hub and the injection needle axially translate along an axis from the retracted position to the injection position;
the injection needle extends through the needle shield aperture in the injection position of the injection needle and the first position of the needle shield, and the injection needle is blocked from extending through the needle shield aperture in the second position of the needle shield; and
when the needle shield is in the second position and the needle hub and the injection needle are in the injection position, the needle shield covers the tip of the injection needle and upon subsequent movement of the needle shield toward the first position, the cantilevered arm axially translates the needle hub and the injection needle back toward the retracted position from the injection position, along the axis.

2. The injector of claim 1, further comprising a biasing member operatively connected with the injection needle to axially translate the needle hub and the injection needle from the retracted position to the injection position.

3. The injector of claim 2, wherein the biasing member applies a biasing force to drive the needle hub and the injection needle from the retracted position to the injection position, and when the needle shield is in the second position and the needle hub and the injection needle are in the injection position, subsequent movement of the needle shield from the second position toward the first position, with a force countering and overcoming the biasing force of the biasing member, axially translates the needle hub and the injection needle back toward the retracted position.

4. The injector of claim 2, wherein the biasing member is a coil spring expandable from a contracted state to an expanded state to axially translate the needle hub and the injection needle from the retracted position to the injection position.

5. The injector of claim 4, wherein when the needle shield is in the second position and the needle hub and the injection needle are in the injection position, subsequent movement of the needle shield toward the first position that axially translates the needle hub and the injection needle back toward the retracted position also compresses the coil spring back toward the contracted state.

6. The injector of claim 4, wherein the injection needle defines a stiffness greater than a stiffness of the coil spring.

7. The injector of claim 1, wherein when the needle shield is in the second position and the needle hub and the injection needle are in the injection position, the needle shield directly contacts the injection needle to axially translate the needle hub and the injection needle back toward the retracted position, upon subsequent movement of the needle shield from the second position toward the first position.

8. The injector of claim 1, wherein when the needle shield is in the second position and the needle hub and the injection needle are in the injection position, subsequent movement of the needle shield toward the first position indirectly axially translates the injection needle back toward the retracted position.

9. The injector of claim 8, wherein the subsequent movement of the needle shield toward the first position engages the cantilevered arm of the needle shield with the needle hub to axially translate the needle hub and the injection needle back toward the retracted position.

10. The injector of claim 1, wherein the needle shield is generally flush with the surface of the injector housing in the first position, and the needle shield is pivoted away from the surface of the injector housing in the second position.

11. The injector of claim 1, wherein the needle shield is biased by a force into the second position thereof.

12. An injector comprising:
an injector housing having a surface configured to contact a skin surface of a user, the surface having an opening therein;
a needle hub movably mounted within the injector housing, wherein the needle hub comprises a flanged member;
an injection needle supported by the movable needle hub, the needle hub and the injection needle being axially translatable between a retracted position, wherein at least a tip of the injection needle is contained within the injector housing, and an injection position, wherein at least the tip of the injection needle protrudes from the injector housing; and
a needle shield having a base surface defining an aperture therein and a cantilevered arm extending from the base surface, the needle shield being movably connected to the injector housing and movable between a first position and a second position, wherein:
the needle hub and the injection needle axially translate along an axis from the retracted position to the injection position;
the injection needle extends through the needle shield aperture in the injection position of the injection needle and the first position of the needle shield, and the injection needle is blocked from extending through the needle shield aperture in the second position of the needle shield; and
when the needle shield is in the second position and the needle hub and the injection needle are in the injection position, the needle shield covers the tip of the injection needle and subsequent movement of the needle shield toward the first position engages the cantilevered arm with the flanged member of the needle hub to axially translate the needle hub and the injection needle back toward the retracted position from the injection position, along the axis.

13. An injector comprising:
an injector housing having a surface configured to contact a skin surface of a user, the surface having an opening therein;
an injection needle movably mounted within the injector housing, the injection needle being axially translatable between a retracted position, wherein at least a tip of the injection needle is contained within the injector housing, and an injection position, wherein at least the tip of the injection needle protrudes from the injector housing; and
a needle shield movably connected to the injector housing and movable between a first position and a second position, the needle shield including an aperture and a cantilevered arm, the cantilevered arm having a flanged free end partially blocking the needle shield aperture, wherein:
the flanged free end clears the injection needle in the first position of the needle shield, permitting the injection needle to extend through the needle shield aperture in the first position of the needle shield; and
when the needle shield is in the second position and the injection needle is in the injection position, the needle shield covers the tip of the injection needle and the flanged free end of the cantilevered arm blocks extension of the injection needle through the needle shield aperture.

14. The injector of claim 13, wherein when the needle shield is in the second position and the injection needle is in the injection position, the flanged free end of the cantilevered arm contacts the tip of the injection needle to axially translate the injection needle back toward the retracted position, upon subsequent movement of the needle shield toward the first position.

15. The injector of claim 13, wherein the cantilevered arm is elastically flexible, and wherein the cantilevered arm is more flexible than the injection needle.

16. The injector of claim 13, wherein when the injection needle is in the injection position, the injection needle engages and elastically flexes the cantilevered arm out of an unflexed resting position thereof during movement of the needle shield from the first position to the second position, and wherein the injection needle disengages the cantilevered arm in the second position of the needle shield, whereby the cantilevered arm returns to the unflexed resting position thereof.

17. The injector of claim 13, wherein when the injection needle is in the injection position, the injection needle engages the flanged free end of the cantilevered arm during movement of the needle shield from the first position to the second position.

18. The injector of claim 13, further comprising a biasing member operatively connected with the injection needle to axially translate the injection needle from the retracted position to the injection position.

19. The injector of claim 18, wherein the biasing member applies a biasing force to drive the injection needle from the retracted position to the injection position, and when the needle shield is in the second position and the injection needle are in the injection position, subsequent movement of the needle shield from the second position toward the first position, with a force countering and overcoming the biasing force of the biasing member, axially translates the injection needle back toward the retracted position.

20. The injector of claim 18, wherein the biasing member is a coil spring expandable from a contracted state to an expanded state to axially translate the injection needle from the retracted position to the injection position.

21. The injector of claim 20, wherein when the needle shield is in the second position and the injection needle is in the injection position, subsequent movement of the needle shield toward the first position that axially translates the injection needle back toward the retracted position also compresses the coil spring back toward the contracted state.

22. The injector of claim 20, wherein the injection needle defines a stiffness greater than a stiffness of the coil spring.

23. The injector of claim 13, wherein the needle shield is generally flush with the surface of the injector housing in the first position, and the needle shield is pivoted away from the surface of the injector housing in the second position.

24. The injector of claim 13, wherein the needle shield is biased by a force into the second position thereof.

25. An injector comprising:
an injector housing having a surface configured to contact a skin surface of a user, the surface having an opening therein;
a needle hub movably mounted within the injector housing;
an injection needle supported by the movable needle hub, the needle hub and the injection needle being axially translatable between a retracted position, wherein at least a tip of the injection needle is contained within the injector housing, and an injection position, wherein at least the tip of the injection needle protrudes from the injector housing;
a needle shield having an aperture, the needle shield being movably connected to the injector housing and movable between a first position and a second position; and
a biasing member operatively connected with the injection needle to axially translate the needle hub and the injection needle from the retracted position to the injection position, wherein:
the needle hub and the injection needle axially translate along an axis from the retracted position to the injection position;
the injection needle extends through the needle shield aperture in the injection position of the injection needle and the first position of the needle shield, and the injection needle is blocked from extending through the needle shield aperture in the second position of the needle shield;
when the needle shield is in the second position and the needle hub and the injection needle are in the injection position, the needle shield covers the tip of the injection needle and subsequent movement of the needle shield toward the first position axially translates the needle hub and the injection needle back toward the retracted position from the injection position, along the axis; and
the injection needle defines a stiffness greater than a stiffness of the biasing member.

26. The injector of claim 25, wherein the biasing member applies a biasing force to drive the needle hub and the injection needle from the retracted position to the injection position, and when the needle shield is in the second position and the needle hub and the injection needle are in the injection position, subsequent movement of the needle shield from the second position toward the first position, with a force countering and overcoming the biasing force of the biasing member, axially translates the needle hub and the injection needle back toward the retracted position.

27. The injector of claim 25, wherein when the needle shield is in the second position and the needle hub and the injection needle are in the injection position, the needle shield directly contacts the injection needle to axially translate the needle hub and the injection needle back toward the retracted position, upon subsequent movement of the needle shield from the second position toward the first position.

28. The injector of claim 25, wherein the needle shield includes a cantilevered arm, the cantilevered arm having a flanged free end partially blocking the needle shield aperture, the flanged free end clearing the injection needle in the first position of the needle shield, and the flanged free end blocking an extension of the injection needle through the needle shield aperture in the second position of the needle shield.

29. The injector of claim 28, wherein when the needle shield is in the second position and the needle hub and the injection needle are in the injection position, the flanged free end of the cantilevered arm contacts the tip of the injection needle to axially translate the needle hub and the injection needle back toward the retracted position, upon subsequent movement of the needle shield toward the first position.

30. The injector of claim 28, wherein the cantilevered arm is elastically flexible, and wherein the cantilevered arm is more flexible than the injection needle.

31. The injector of claim 28, wherein when the injection needle is in the injection position, the injection needle engages and elastically flexes the cantilevered arm out of an unflexed resting position thereof during movement of the needle shield from the first position to the second position, and wherein the injection needle disengages the cantilevered arm in the second position of the needle shield, whereby the cantilevered arm returns to the unflexed resting position thereof.

32. The injector of claim 28, wherein when the injection needle is in the injection position, the injection needle engages the flanged free end of the cantilevered arm during movement of the needle shield from the first position to the second position.

33. The injector of claim 25, wherein when the needle shield is in the second position and the needle hub and the injection needle are in the injection position, subsequent movement of the needle shield toward the first position indirectly axially translates the injection needle back toward the retracted position.

34. The injector of claim 33, wherein the needle shield comprises an arm, and wherein when the needle shield is in the second position and the needle hub and the injection needle are in the injection position, subsequent movement of the needle shield toward the first position engages the arm of the needle shield with the needle hub to axially translate the needle hub and the injection needle back toward the retracted position.

35. The injector of claim 34, wherein the needle hub comprises a flanged member, and wherein when the needle shield is in the second position and the needle hub and the injection needle are in the injection position, subsequent movement of the needle shield toward the first position engages the needle shield arm with the flanged member of the needle hub to axially translate the needle hub and the injection needle back toward the retracted position.

36. The injector of claim 34, wherein the arm is a cantilevered arm, a flanged free end of the arm being configured to engage with the needle hub.

37. The injector of claim 25, wherein the needle shield is generally flush with surface of the injector housing in the first position, and the needle shield is pivoted away from the surface of the injector housing in the second position.

38. The injector of claim 25, wherein the needle shield is biased by a force into the second position thereof.

39. The injector of claim 25, wherein the biasing member is a coil spring expandable from a contracted state to an expanded state to axially translate the needle hub and the injection needle from the retracted position to the injection position.

40. The injector of claim 39, wherein when the needle shield is in the second position and the needle hub and the injection needle are in the injection position, subsequent movement of the needle shield toward the first position that axially translates the needle hub and the injection needle back toward the retracted position also compresses the coil spring back toward the contracted state.

\* \* \* \* \*